United States Patent
Rabinne et al.

(10) Patent No.: US 9,345,846 B1
(45) Date of Patent: May 24, 2016

(54) MOLDING APPARATUS, METHOD AND SYRINGE PRODUCED USING SAME

(71) Applicants: Bruce Rabinne, Boissy-le-Chatel (FR); Bernard Sol, Maisons-Alfort (FR); Jean-Pierre Giraud, Auburn, AL (US)

(72) Inventors: Bruce Rabinne, Boissy-le-Chatel (FR); Bernard Sol, Maisons-Alfort (FR); Jean-Pierre Giraud, Auburn, AL (US)

(73) Assignee: SIO2 MEDICAL PRODUCTS, INC., Auburn, AL (US)

( * ) Notice: Subject to any disclaimer, the term of this patent is extended or adjusted under 35 U.S.C. 154(b) by 0 days.

(21) Appl. No.: 13/894,984

(22) Filed: May 15, 2013

Related U.S. Application Data

(60) Provisional application No. 61/647,204, filed on May 15, 2012.

(51) Int. Cl.
*B29C 45/14* (2006.01)
*A61M 5/34* (2006.01)
*A61M 5/32* (2006.01)
*A61M 5/31* (2006.01)
*B29C 45/33* (2006.01)
*B29L 31/00* (2006.01)

(52) U.S. Cl.
CPC .................. *A61M 5/34* (2013.01); *B29C 45/14* (2013.01); *A61M 5/3134* (2013.01); *A61M 5/3293* (2013.01); *A61M 5/343* (2013.01); *B29C 45/14065* (2013.01); *B29C 45/33* (2013.01); *B29C 45/332* (2013.01); *B29L 2031/7544* (2013.01)

(58) Field of Classification Search
CPC . A61M 5/3134; A61M 5/3293; A61M 5/343; B29L 2031/7544; B29C 45/33; B29C 45/332; B29C 45/14; B29C 45/14065

USPC ............... 264/271.1, 275; 425/123, 589, 317, 425/414, 416, 126.1, 552; 604/239, 240
See application file for complete search history.

(56) References Cited

U.S. PATENT DOCUMENTS

| | | | | |
|---|---|---|---|---|
| 7,481,648 B1 * | 1/2009 | Chen | ....................... | B29C 33/44 425/441 |
| 7,568,906 B2 * | 8/2009 | Kmoch | ............... | B29C 45/2711 425/547 |
| 2010/0270702 A1 * | 10/2010 | Zelkovich | ............. | A61M 5/343 264/278 |
| 2011/0037197 A1 * | 2/2011 | Trascinelli | ........... | B29C 45/0062 264/246 |
| 2013/0200549 A1 * | 8/2013 | Felts | ................... | A61M 5/3129 264/275 |
| 2014/0070453 A1 * | 3/2014 | Dietl | ....................... | A61M 5/34 264/275 |

* cited by examiner

*Primary Examiner* — Alison L Hindenlang
*Assistant Examiner* — Lawrence D Hohenbrink, Jr.
(74) *Attorney, Agent, or Firm* — McAndrews, Held & Malloy, Ltd.

(57) ABSTRACT

A molding assembly for molding a syringe with a needle embedded therein includes a first mold portion and a second mold portion. The second mold portion includes a molding block, an end plate and a needle holding block configured to hold the needle. The assembly moves between an opened position in which the first mold portion is displaced from the second mold portion, and a closed position in which the molding block and the end plate define a molding cavity configured to form a body portion of the syringe, and the first mold portion contacts the second mold portion to hold the needle holding block adjacent to the molding cavity, such that the needle is partially positioned within the molding cavity.

40 Claims, 20 Drawing Sheets

MOLDING APPARATUS, METHOD AND SYRINGE PRODUCED USING SAME

Priority is claimed of U.S. Provisional Application Ser. No. 61/647,204, filed May 15, 2012. This application is incorporated here by reference in its entirety.

FIELD OF INVENTION

The present invention is directed to a molding assembly and a molding method, and in particular a molding assembly and method suitable for producing a syringe body. The present invention is further directed to a syringe produced using such a molding assembly and method.

SUMMARY

The invention pertains to a molding assembly for molding a syringe with a needle embedded therein. The assembly includes a first mold portion and a second mold portion. The second mold portion includes a molding block, an end plate and a needle holding block configured to hold the needle. The assembly moves between an opened position in which the first mold portion is displaced from the second mold portion, and a closed position in which the molding block and the end plate define a molding cavity configured to form a body portion of the syringe, and the first mold portion contacts the second mold portion to hold the needle holding block adjacent to the molding cavity, such that the needle is partially positioned within the molding cavity.

The invention further relates to a method of molding a syringe using such a molding assembly. The method includes providing the molding assembly in the opened position, moving the molding assembly into the closed position by moving the first mold portion into contact with the second mold portion and locating a portion of the needle within the molding cavity, and injecting a molding material into the molding cavity. The method further includes cooling the molding material to solidify the molding material and produce a syringe body with the needle embedded therein, moving the molding assembly into the opened position, and removing the syringe body from the molding assembly.

The invention further pertains to a syringe produced using such a molding assembly or method. The syringe includes a barrel formed as a substantially tubular wall having a first, opened end leading to an interior and a second, closed end, a hub extending outward from the second end, and a needle extending through the hub, the needle having a first, staked end for injecting into a patient, and a second end located on the interior and flush with an inner surface of the barrel.

DETAILED DESCRIPTION OF THE PREFERRED EMBODIMENTS

Figure 1:
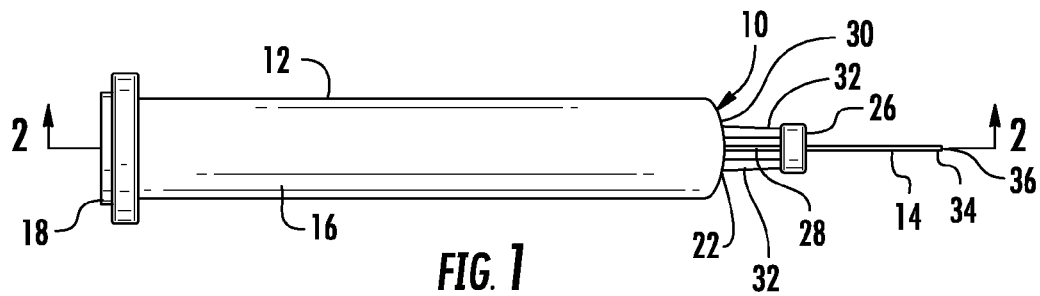
FIG. 1 is a side elevational view of a syringe body in accordance with the invention.

Certain terminology is used in the foregoing description for convenience and is not intended to be limiting. Words such as "front," "back," "top," and "bottom" designate directions in the drawings to which reference is made. This terminology includes the words specifically noted above, derivatives thereof, and words of similar import. Additionally, the words "a" and "one" are defined as including one or more of the referenced item unless specifically noted. The phrase "at least one of" followed by a list of two or more items, such as "A, B or C," means any individual one of A, B or C, as well as any combination thereof.

Figure 2:
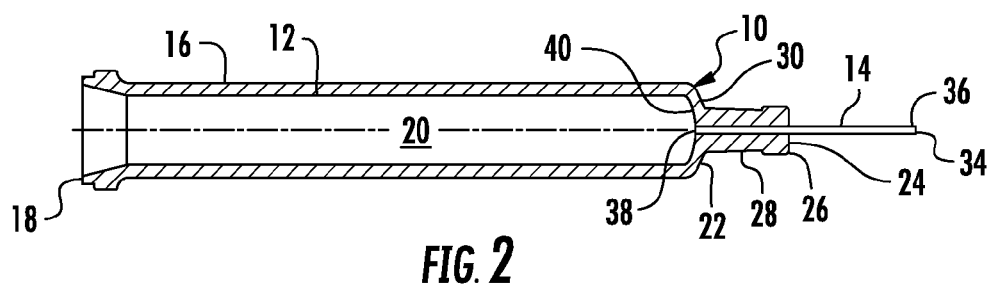
FIG. 2 is a cross section taken along line 2-2 of FIG. 1.
Figure 3:
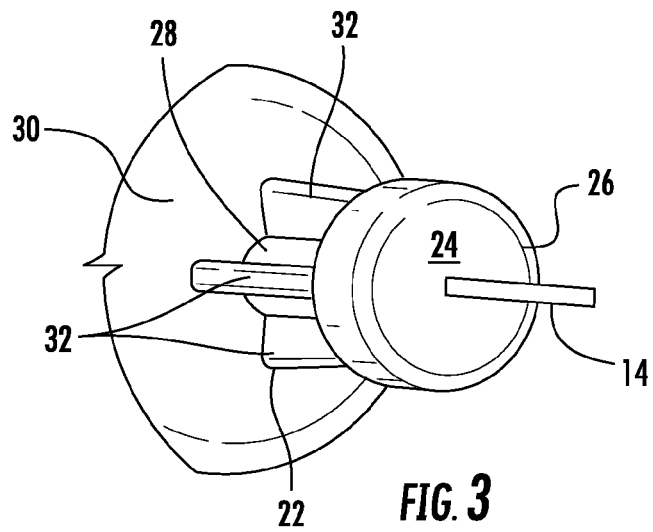
FIG. 3 is an enlarged perspective view of the hub region of the syringe body of FIG. 1.

An embodiment of a syringe body 10 according to the invention is shown in FIGS. 1-3. The syringe body 10 includes a barrel 12 and a needle 14. The barrel 12 is formed as a substantially tubular wall 16 with an opened first end 18 leading to an interior 20. In use, a plunger would be slidably housed within the interior 20 and partially protruding outward from the opened first end 18. A needle receiving hub 24 protrudes from the second end 22 of the barrel 12, outward from an outward convexly curved end wall 30. The needle 14 extends through the hub 24 from the exterior to the interior 20 of the hub 24, for transmission of an injectable material out from the syringe body 10 and into a patient. In the illustrated embodiment, the hub 24 includes a needle holding band 26 that is displaced from the barrel 12 and a tube 28 joining the band 26 with the second end 22 of the barrel 12. A plurality of fins 32 may extend radially outward from the tube 28, between the band 26 and the end wall 30, in order to impart rigidity on the tube 28. Four fins 32 are provided in the illustrated embodiment, though fewer or more fins 32 could be provided as well. The needle 14 includes a first end 34 having a staked tip 36 and a second end 38 located on the interior of the barrel 12 that is substantially flush with the inner surface 40 of the end wall 30. As shown in FIG. 2, the needle 14 passes through the end wall 30, and is embedded in the material that forms the barrel 12. This can be achieved by inserting the needle 14 into the molding cavity during molding of the syringe body 10, as described in detail below. A cap that engages the barrel 12 to cover the needle 14 and protect a user from the sharp, staked tip 36 when not using the syringe may optionally be provided.

A first embodiment of a molding assembly 100 for molding a syringe body 10 in accordance with the invention is shown in FIGS. 4-19. The molding assembly 100 is suitable for molding a syringe body 10 having an integrated needle 14 that is embedded in the material of the barrel 12, as described in detail below. The molding assembly 100 includes a lower or fixed portion 130 and a mobile, upper portion 110.

Figure 5:
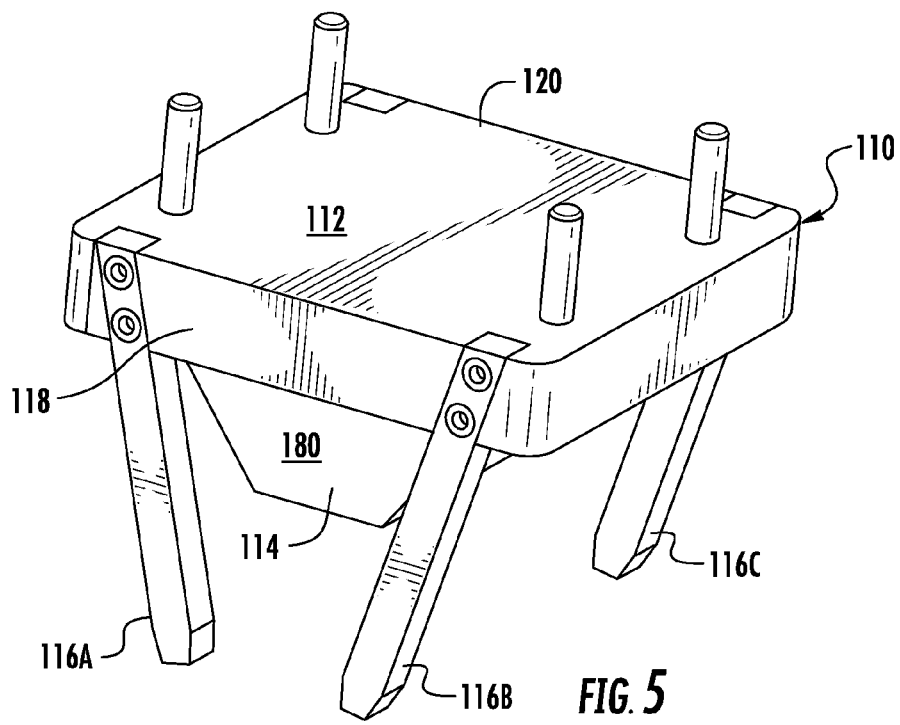
FIG. 5 is a top perspective view of the upper portion of the molding assembly of FIG. 4, in a closed position.
Figure 6:
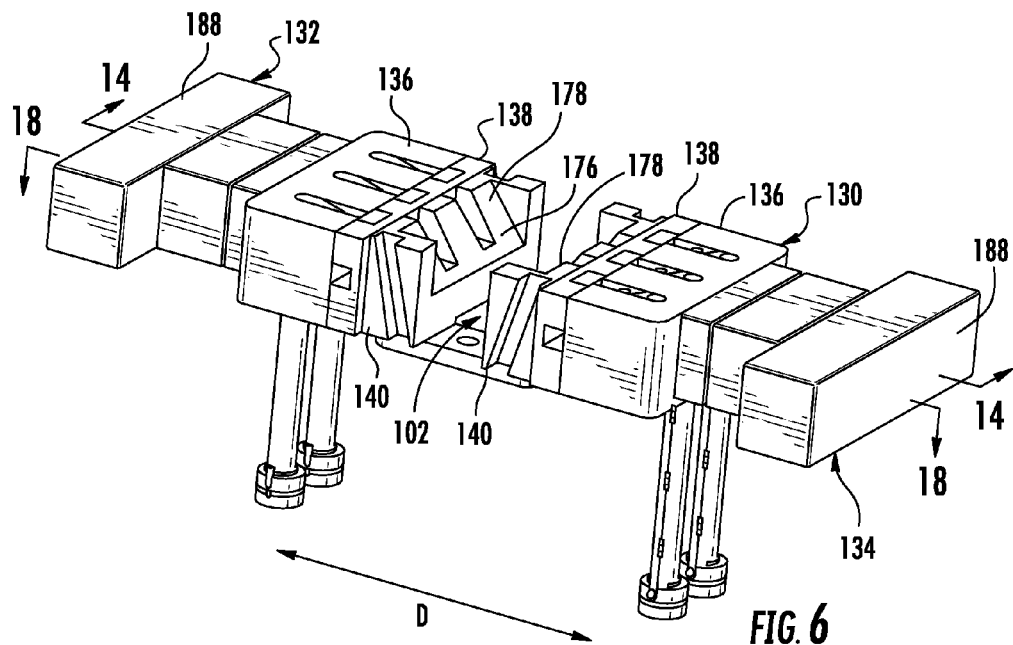
FIG. 6 is a top perspective view of the fixed portion of the molding assembly of FIG. 4, in a closed position.
Figure 7:
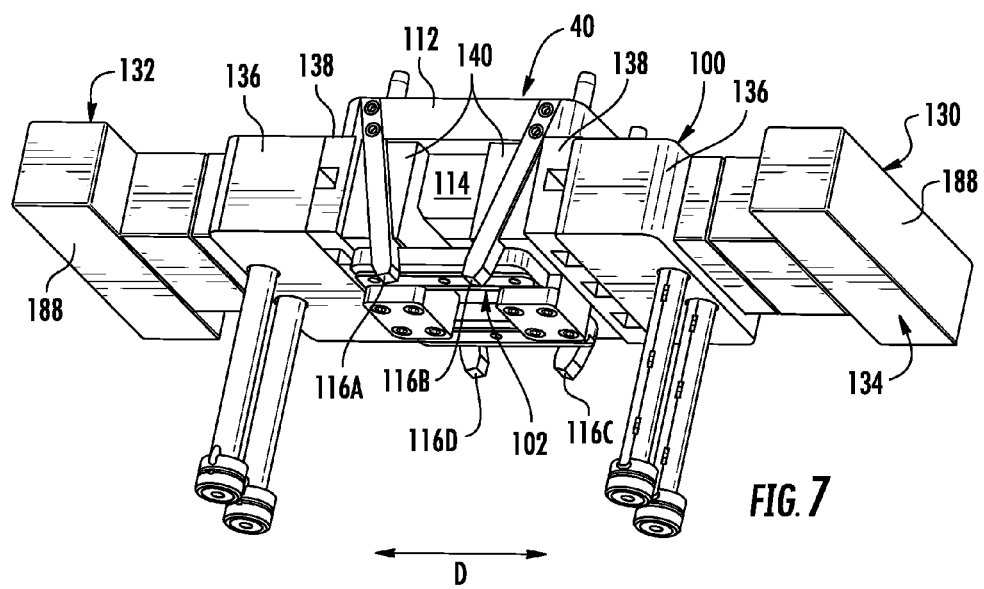
FIG. 7 is a bottom perspective view of the molding assembly of FIG. 4, in a closed position.
Figure 8:
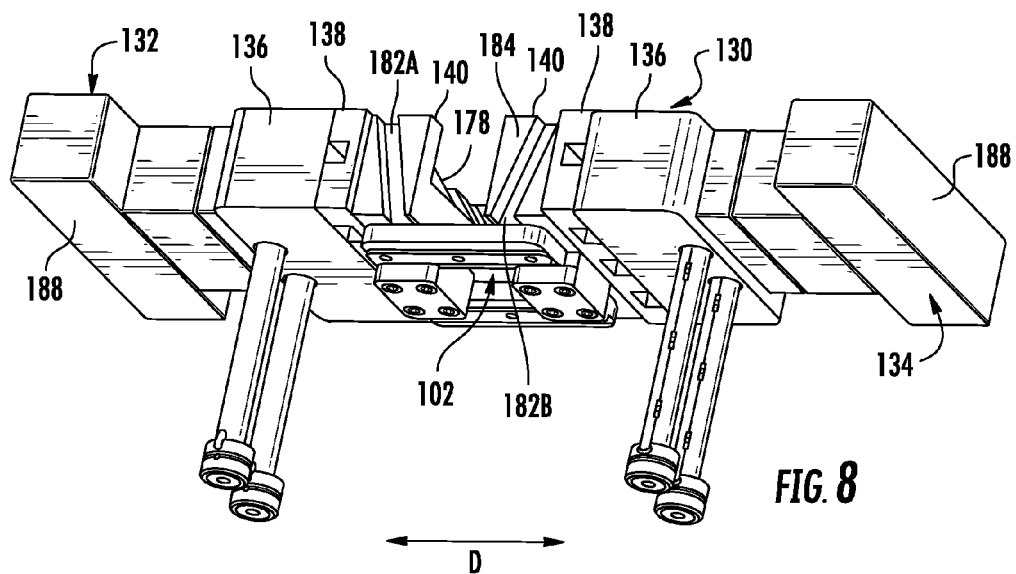
FIG. 8 is a bottom perspective view of the fixed portion of the molding assembly of FIG. 4, in a closed position.
Figure 9:
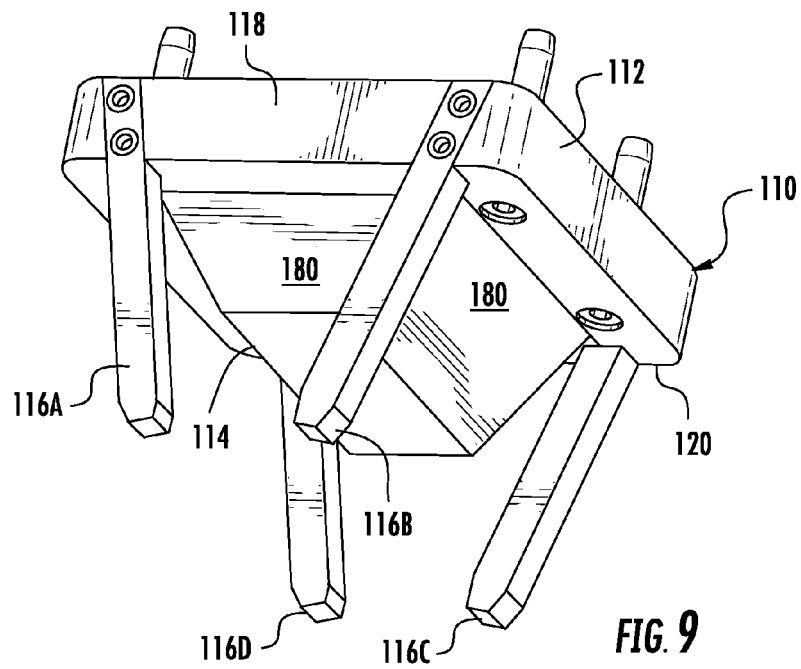
FIG. 9 is a bottom perspective view of the upper portion of the molding assembly of FIG. 4, in a closed position.
Figure 11:
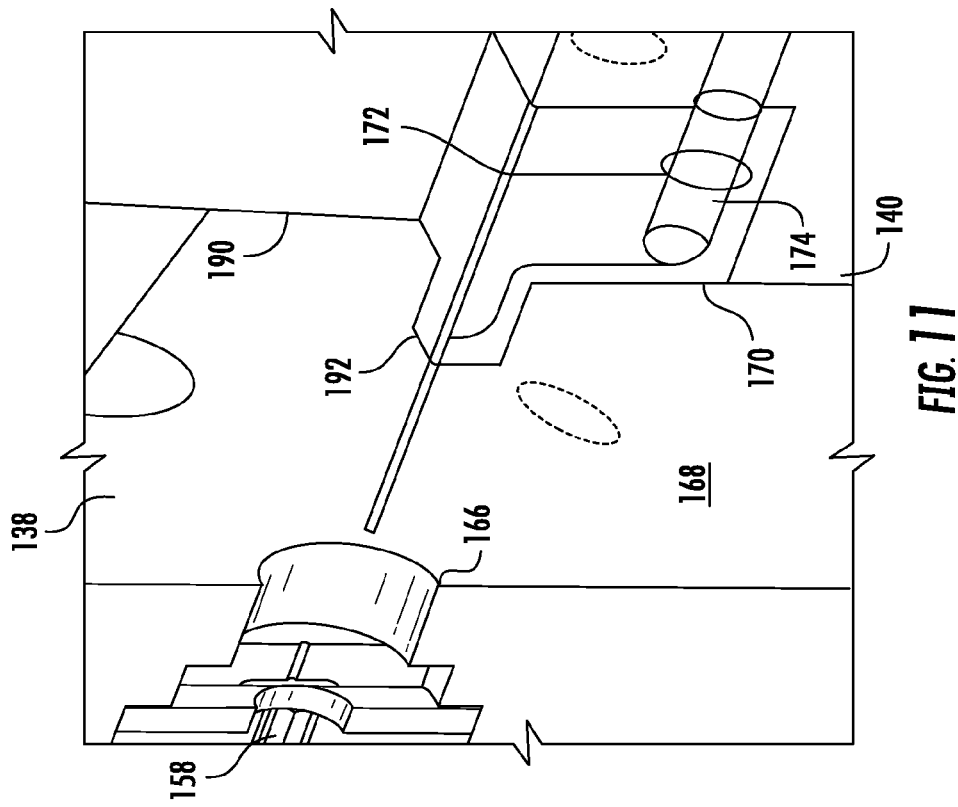
FIG. 11 is an enlarged detail of FIG. 10.

The upper portion 110 is shown in detail in FIGS. 5 and 9. As shown, the upper portion 110 includes a top plate 112 that extends is a substantially horizontal, planar orientation. A plug member 114 extends downward from a bottom surface of the top plate 112. The plug member 114 is shaped as an inverted frusto-pyramid, with the planar base thereof adjoined with the bottom surface of the top plate 112, and the frusto-pyramidal shape tapering inward as it extends downward. Four guide posts 116A-D extend downward from the top plate, about the four corners thereof in the illustrated embodiment. Two of the posts 116A, 116B are located on a front side 118 of the upper portion 110 and two of the posts 116C, 116D are located on a rear side 120 of the upper portion. Posts 116A, 116B extend downward and towards each other within a vertical plane extending downward from the front side 118, and posts 116B, 116D extend downward and towards each other within a vertical plane extending downward from the rear side 120.

The lower or fixed portion 130 is shown in detail in FIGS. 6, 8 and 10-19. As shown, the lower portion 130 includes a first side 132 and a second side 134. The first and second sides 132, 134 are mirror images of each other, and the first side 132 will be described in detail, though it should be understood that the second side 134 includes each of the elements described as well, oriented in a mirror image configuration with respect to those of the first side 132.

The first side 132 includes a molding or outer block 136, an end plate 138 and a needle insertion block 140. The components are arranged such that the outer block 136 is located towards an outer end of the lower portion 130, the needle insertion block 140 is located towards an opposite end thereof, and the end plate 138 is located between the two. In this manner, the outer blocks 136 of the first and second sides 132, 134 are located outward of the end plates 138, which are located outward of the centrally located needle insertion blocks 140.

Figure 10:
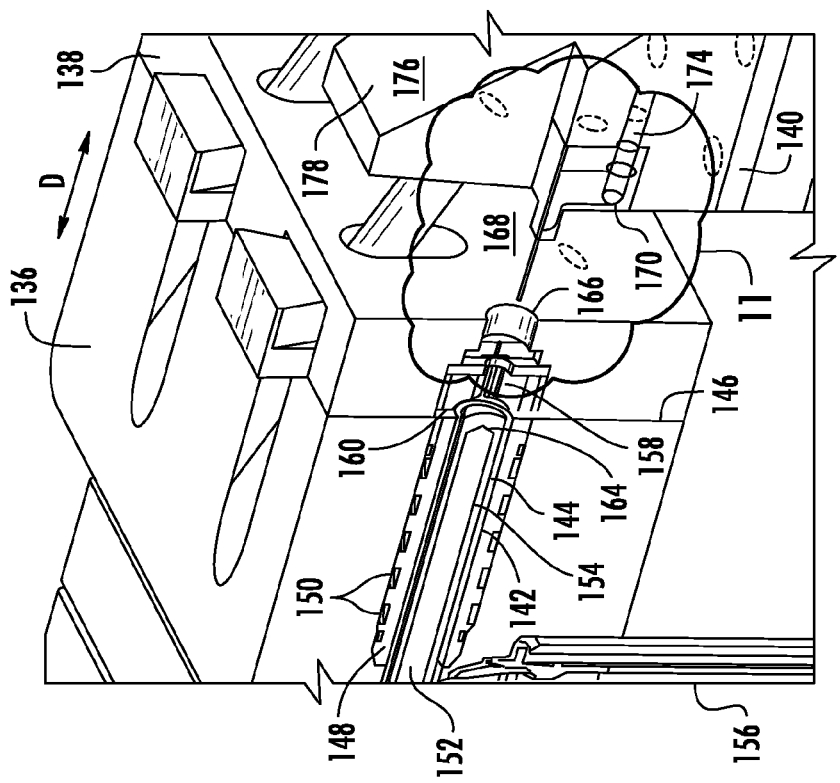
FIG. 10 is a partially cut away perspective view of the fixed portion of the molding assembly of FIG. 4, in an opened position.
Figure 13:
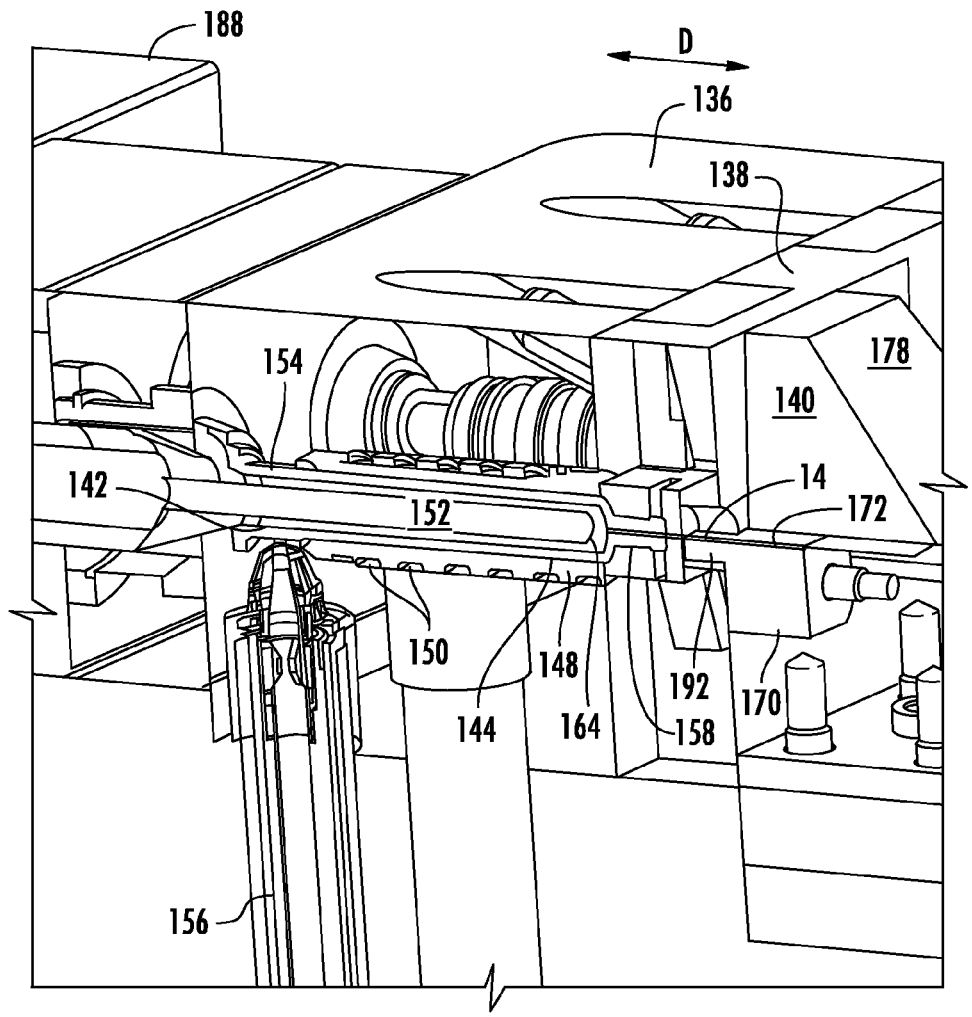
FIG. 13 is an enlarged detail of FIG. 12.
Figure 14:
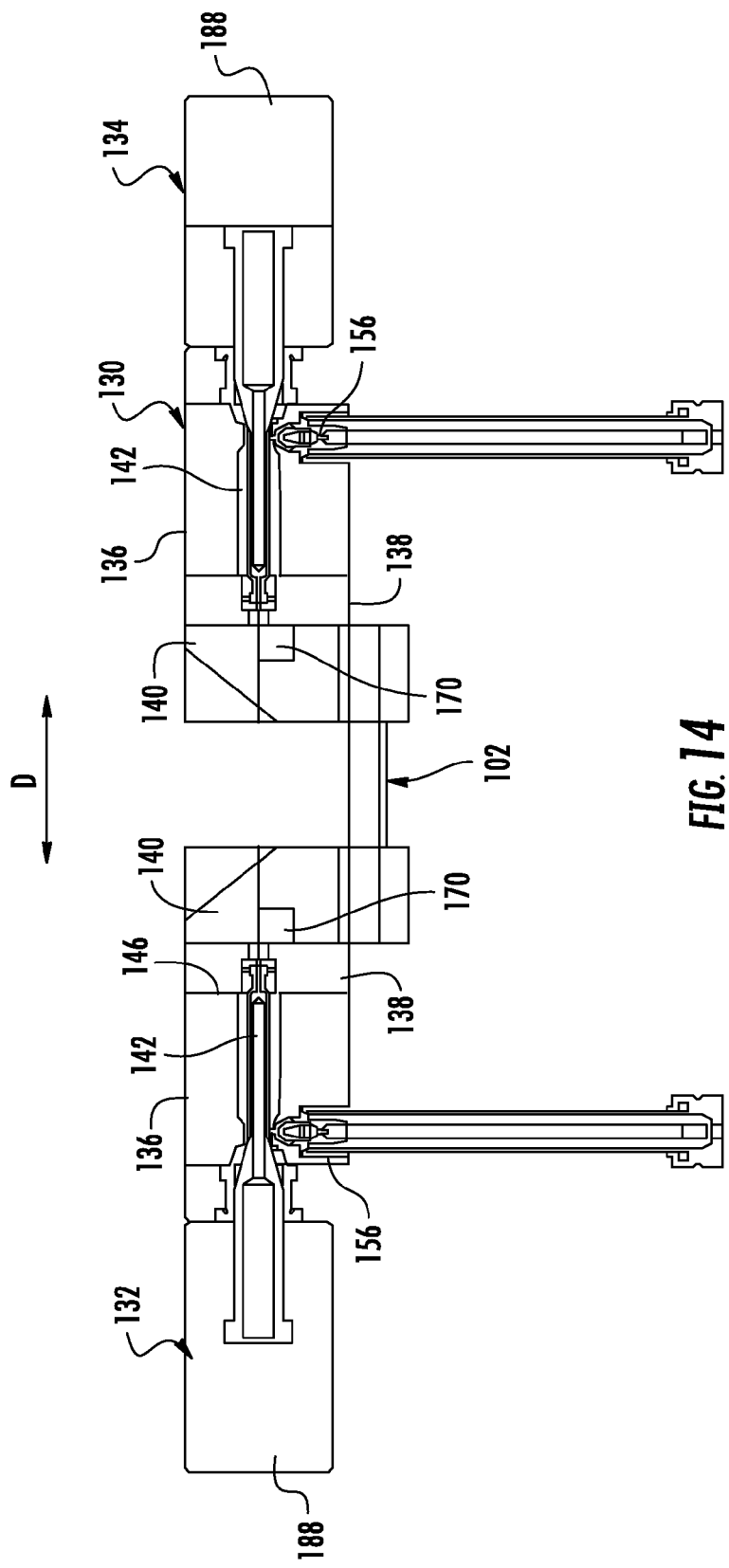
FIG. 14 is a cross section taken along line 14-14 of FIG. 6.

The outer block 136 defines a plurality of molding cavities 142. In the illustrated embodiment, the each of the outer blocks 132 defines two molding cavities 142, such that the entire molding assembly 100 includes four molding cavities 142. It should be understood that fewer or more molding cavities 142 could be provided while remaining within the scope of the invention. The molding cavities 142, shown in detail in FIGS. 10 and 13, are configured for molding a syringe barrel 12 of the type shown in FIGS. 1-3. Each molding cavity 142 is formed as a cylindrical opening 144 in the outer block 132. The opening 144 extends in direction D to an inner surface 146 of the outer block 136 that faces towards the center 102 of the molding assembly 100. A sleeve 148 may be fitted within the outer block 132 and define the opening 144. The sleeve 148 is formed of a material capable of appropriately distributing heat during molding and may include a plurality of cooling channels 150.

An inner core 152 fits within the opening 144 to define the interior 20 of the syringe body 10. The inner core 152 is of a cylindrical shape similar to that of the opening 144, but is of a smaller diameter. A molding space 154 is defined between the opening 144 and the inner core 152. The molding space 154 is sized and shaped to form a syringe barrel 12, such as that shown in FIGS. 1-3. The inner core 152 projects from a core plate 188, which is located outward in the molding assembly 100 with respect to the outer block 136.

An injector 156 extends through a portion of outer block 136 for injecting molding material into the molding cavity 142 during molding.

Figure 12:
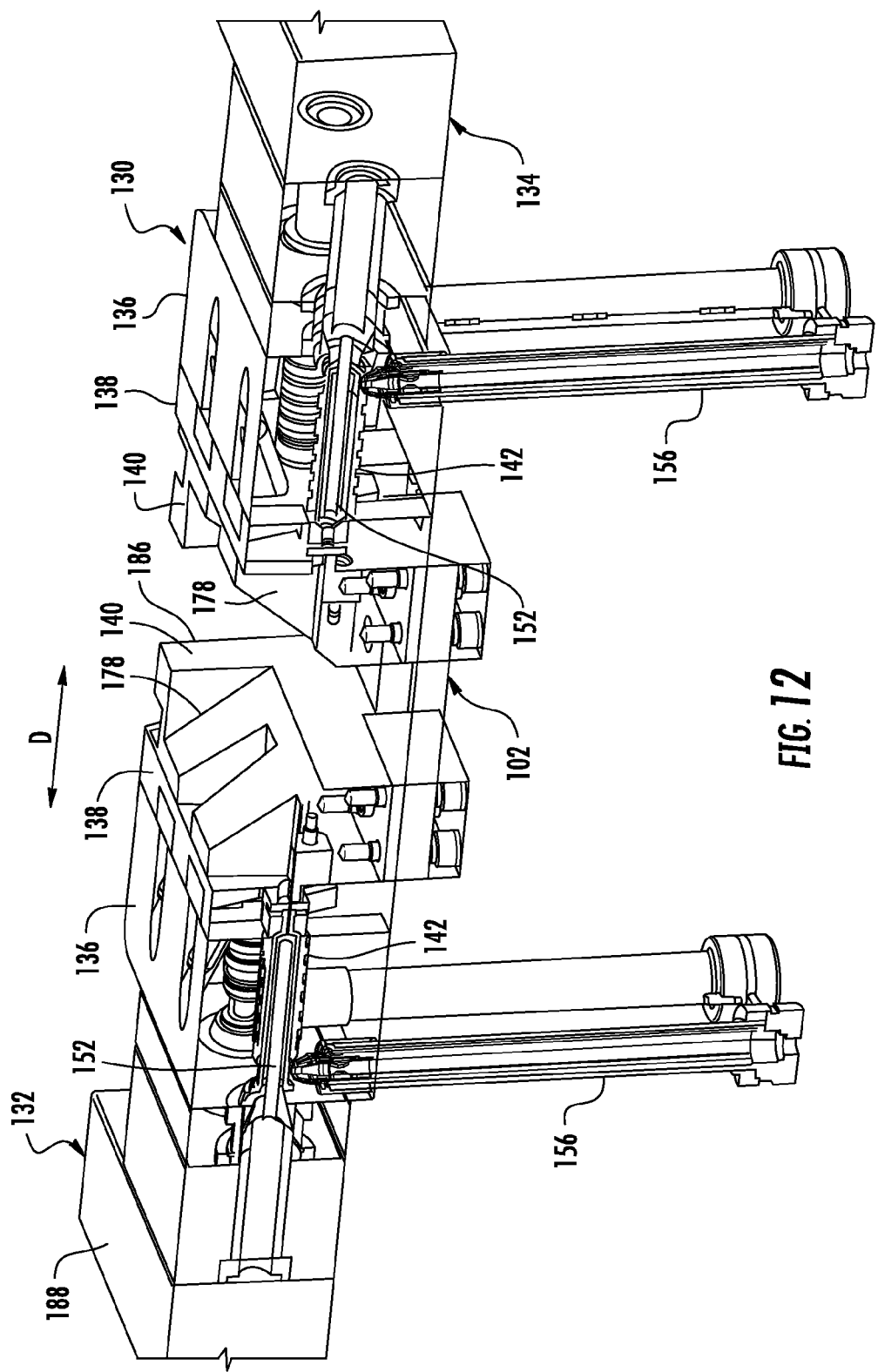
FIG. 12 is a partially cut away perspective view of the fixed portion of the molding assembly of FIG. 4, in a closed position.

The end plate 138 is shown in detail in FIGS. 10-13. The end plate 138 is formed as a vertically extending, planar wall that abuts the inner surface 146 of outer block 136 when the molding assembly 100 is in a closed position, as shown in FIGS. 12 and 13. The end plate 138 defines a hub cavity 158 that forms the hub 24 of the syringe body 10. Hub cavity 158 includes an outer opening 160 defined on the outer surface 162 of the end plate 138, which faces towards the outside of the molding assembly 100 and abuts inner surface 146 of outer block 136. Hub cavity 158 is axially aligned with molding cavity 142, to define a continuous, barrel-shaped cavity for forming the syringe barrel 12. The portion of molding space 154 that forms the barrel end wall 30 is defined between curved portions of the end plate outer surface 162 and the end 164 of core 152. The hub cavity 158 is sized and shaped to form needle hub 24, including needle holding band 26, tube 28, and fins 32. Hub cavity 158 extends all the way through end plate 138, to an inner opening 166 formed on an inner surface 168 of end plate 138, which faces inward with respect to the molding assembly 100.

The needle holding block 140 is located inward of the outer block 136 and end plate 138. A needle grip 170 is housed within an opening formed on an outer surface 190 of the needle holding block 140, which faces outward with respect to the molding assembly 100. The needle grip 170 includes a projection 192 sized and shaped to be received by inner opening 166 of end plate 138. The needle grip 170 includes a needle opening 172 that extends through projection 192 and is sized and shaped to receive a portion of the needle 14 located towards the first end 34 thereof, but is sufficiently large so as to not create an interference fit between the needle 14 and the opening 172, so as to allow some sliding of the needle 14, as described below. The needle opening 172 is axially aligned with the molding cavity 142 when the molding assembly 100 is in the closed position.

A vacuum channel 174 extends through the needle holding block 140 and is in communication with the needle opening 172.

Figure 4:
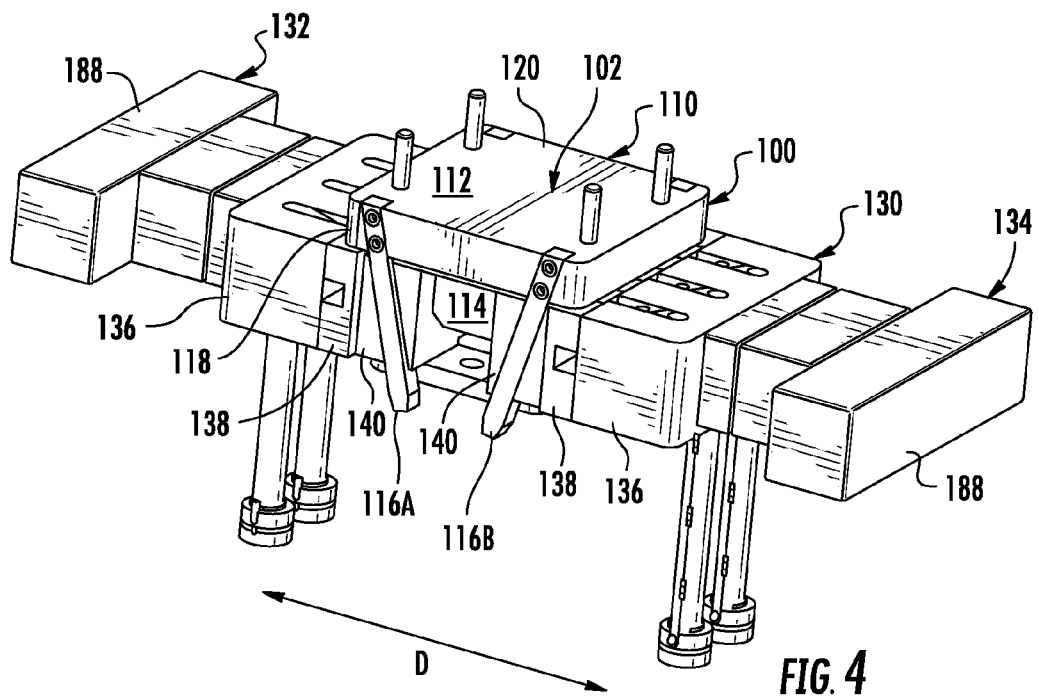
FIG. 4 is a top perspective view of a first embodiment of a molding assembly according to the invention, in a closed position.

The inner surface 176 of the needle holding block 140, which faces inward with respect to the molding assembly 100, includes a sloped side 178 that is complementary with one of the four sides 180 forming the frusto-pyramidal shape of the plug member 114. In the illustrated embodiment, the two needle holding blocks 140 of the assembly 100 are oriented to abut two opposite sides 180 of the plug member 114. In other embodiments, the needle holding blocks 140 could be oriented to abut adjacent sides 114. In yet other embodiments, a single needle holding block 140 could be employed, or three or four needle holding blocks 140 could be employed and positioned to abut the front or rear sides 180 of the plug member 180, located between those utilized in the illustrated embodiment. Grooves 182 extend downward along the front 184 and rear 186 sides of the needle holding block 140. Grooves are generally linear and extend in the same direction as posts 116 of the upper portion 110. In the assembled configuration, posts 116 sit within grooves 182, as shown in FIG. 4.

A syringe body 10 in accordance with the invention is molded using the molding assembly 100 as follows. The upper portion 110 of the assembly 100 is initially held in a raised position with respect to the fixed portion 130. The engagement of posts 116 within grooves 182, and the inwardly extending angle of both with respect to the assembly 100, results in the needle holding blocks being held at first positions towards the center 102 of the assembly in direction D, and in turn displaced from end plate 138. A needle 14 is placed within the opening 172 of the needle grip 170, oriented with the first end 34 having the staked tip 36 pointing towards the center 102 of the assembly 100 in direction D, and the second end 38 pointing outwards with respect to the assembly 100, towards the end plate 138. At this time, core plate 188 is located outward of the assembly in direction D, and core 152 is located outside of opening 144.

Figure 15:
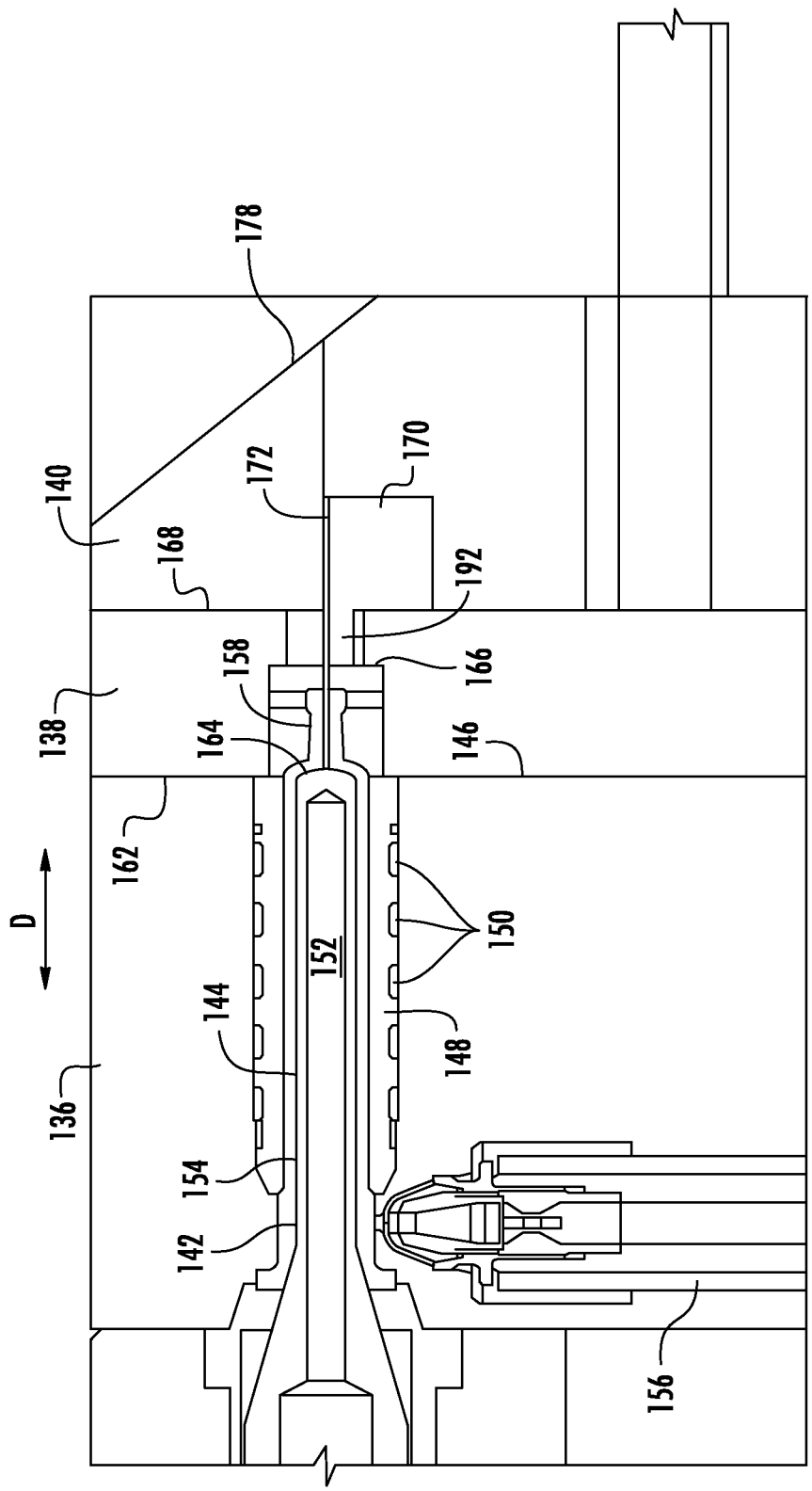
FIG. 15 is an enlarged detail of FIG. 14.
Figure 16:
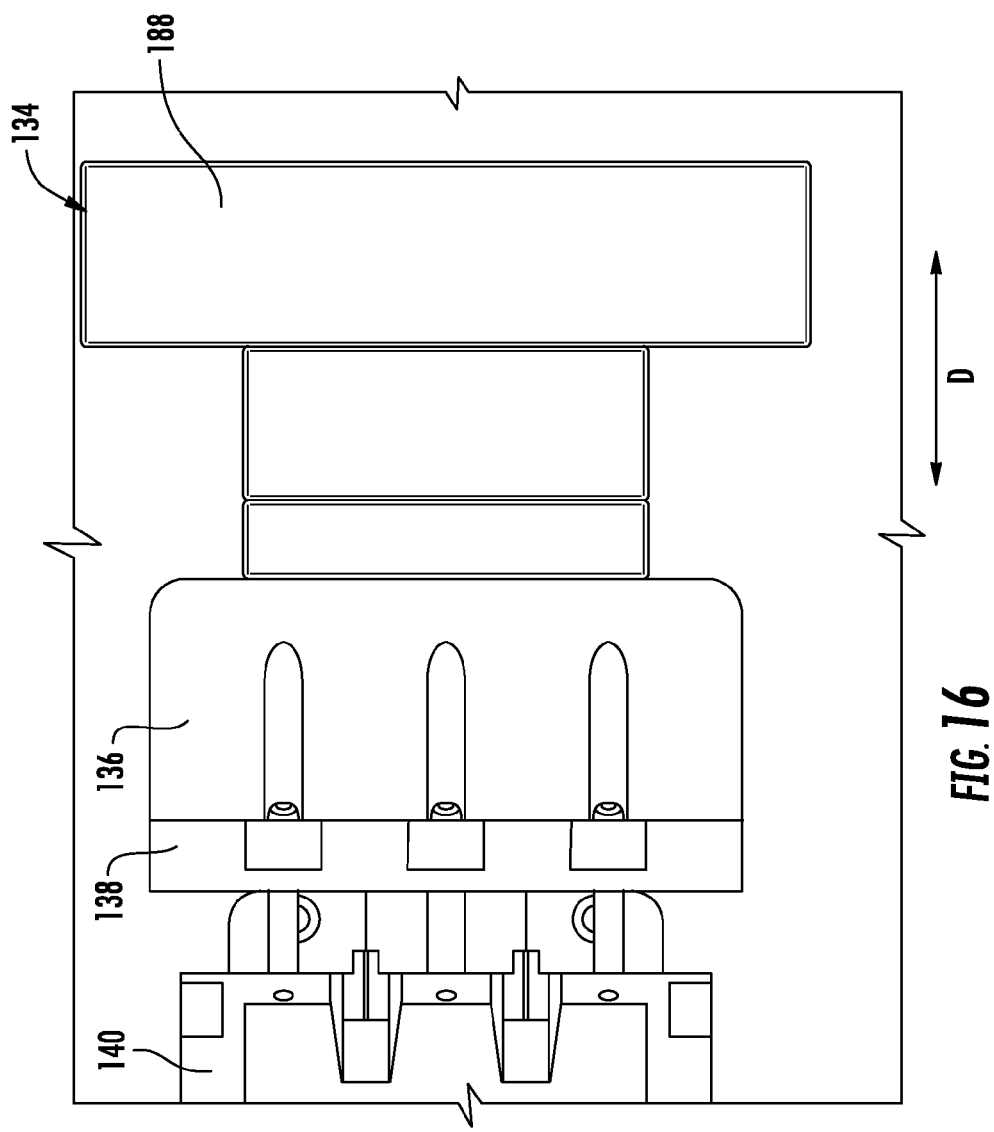
FIG. 16 is a top perspective view of a portion of the fixed portion of the molding assembly of FIG. 4, in the opened position.
Figure 17:
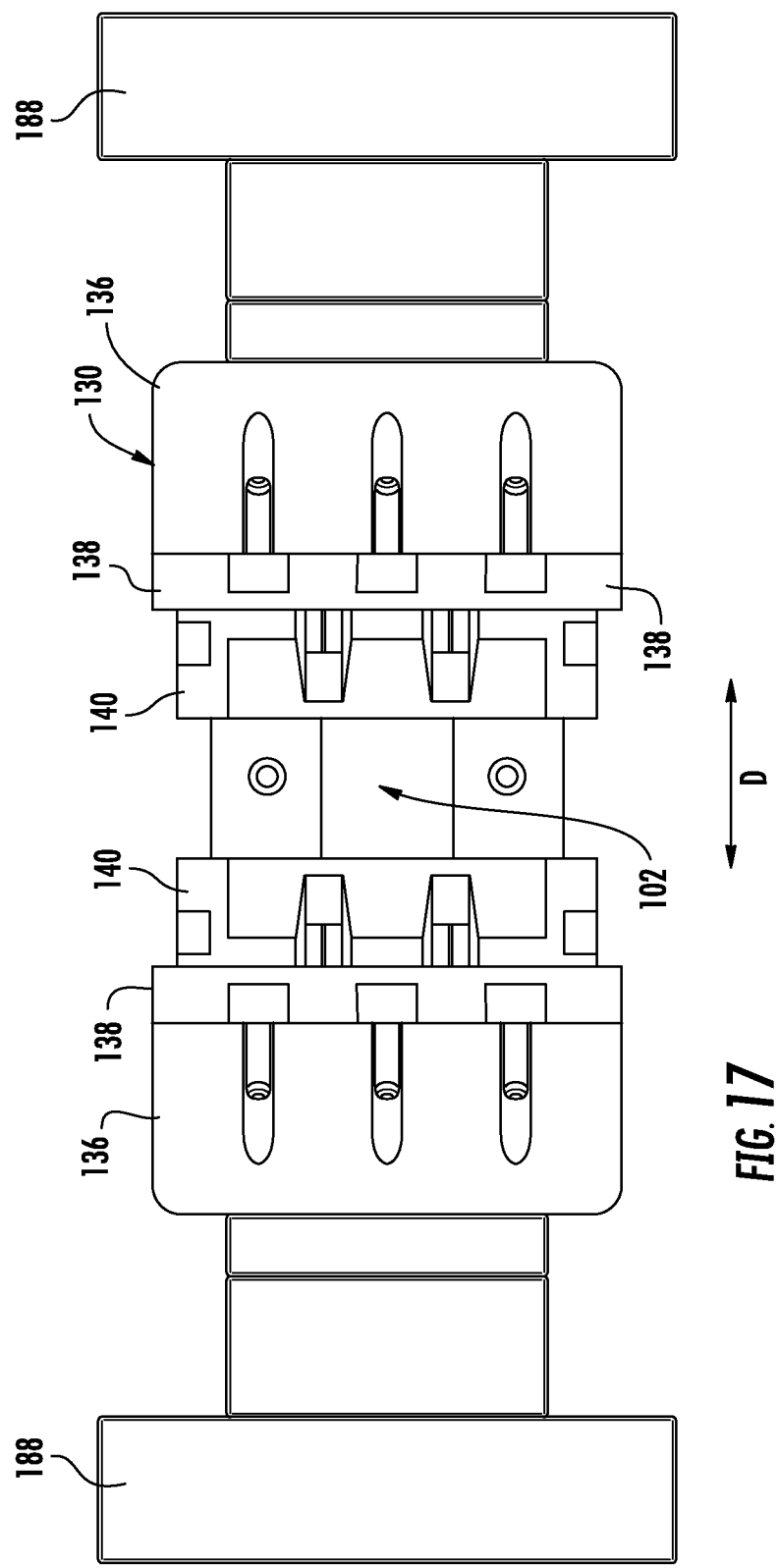
FIG. 17 is a top perspective view of the fixed portion of the molding assembly of FIG. 4, in the closed position.
Figure 18:
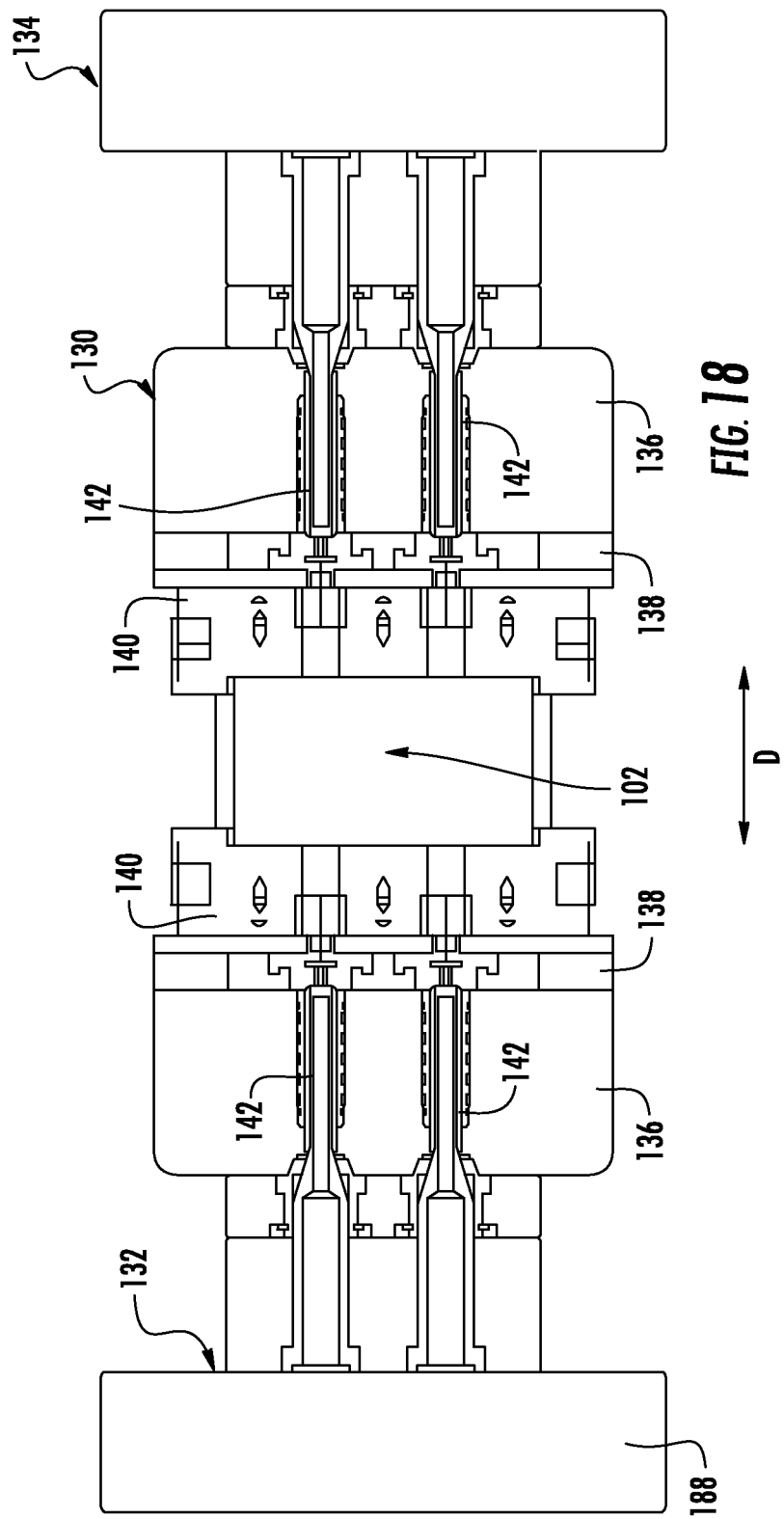
FIG. 18 is a cross section taken along line 18-18 of FIG. 6.
Figure 19:
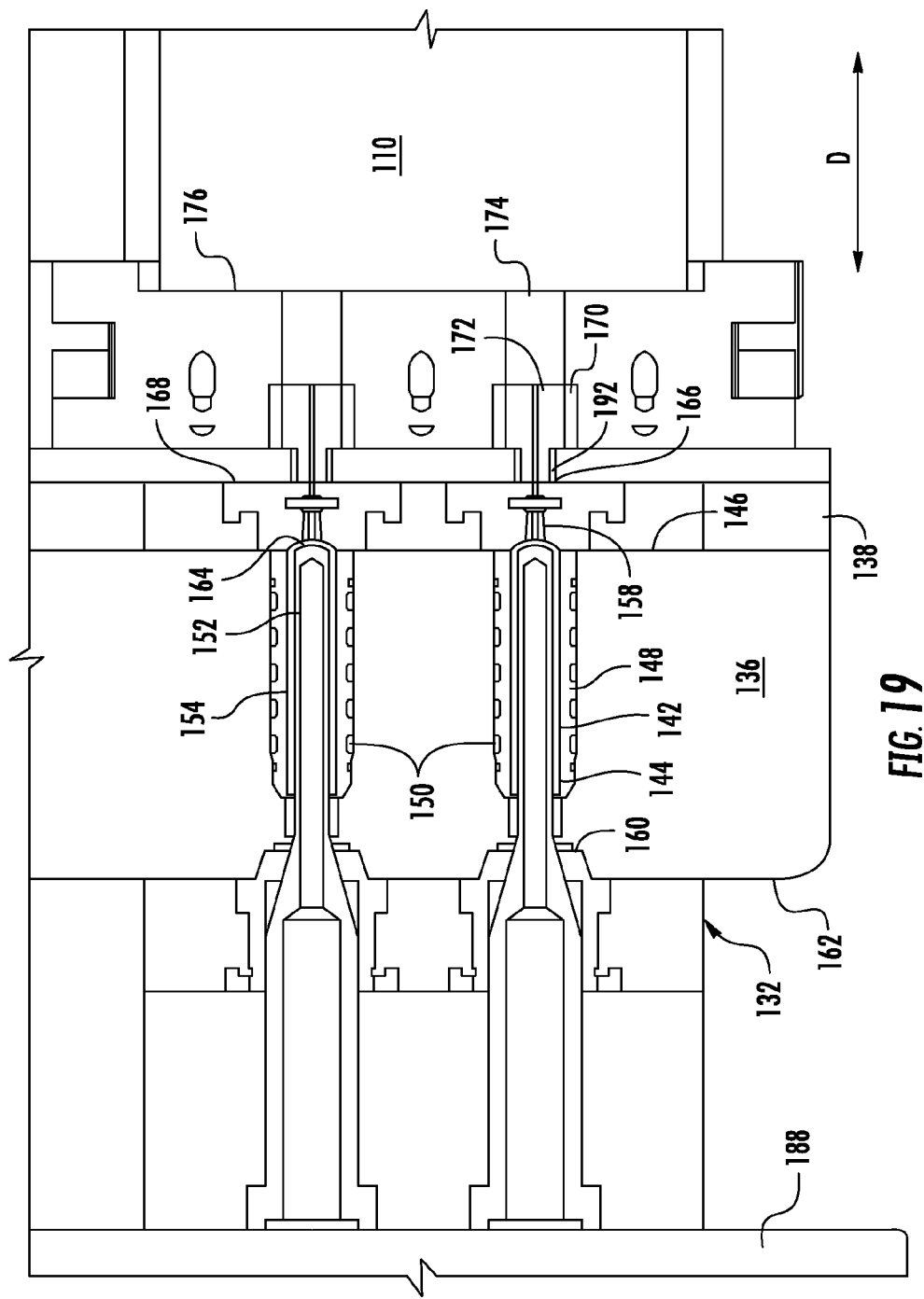
FIG. 19 is an enlarged detail of FIG. 18.

Upon initiation of a molding operation, core plate 188 is first moved towards the center 102 of the assembly in direction D, such that core 152 is moved into opening 144, to create a syringe barrel 12 shaped molding space 154. After the core 152 is in position, the needle 14 is moved into a molding position, as shown in FIGS. 13 and 15. During this time a vacuum is applied to opening 172 through vacuum channel 174. This vacuum slidably secures needle 14 within opening 172. To move the needle 14 into the molding position, upper portion 110 of the molding assembly 100 is moved downward, towards the fixed portion 130. Engagement of posts 116 with grooves 182 and the angled orientation of both causes posts 116 to drive the needle block 140 outward in direction D, away from the center 102 of the assembly 100. This in turn results in the needle grip 170 and the needle 14 held therein being moved towards the outer block 136 and end plate 138, which define the molding cavity 142. Sloped sides 178 of needle holding block 140 maintain contact with sides 180 of plug member 114. Needle 14 is continuously moved until it comes into abutment with core 152, as shown in FIGS. 13 and 15. The slidability of needle 14 within opening 172 allows needle 14 to be precisely positioned against core 152, as needle grip 170 can continue to move in direction D towards the center 102 of the assembly 100 after needle 14 has come into position and is prevented from further movement by the core 152. Needle grip 170 continues to move outward in direction D, until projection 192 is received within inner opening 166 of end plate 138, closing off the molding cavity 142 and the molding space 154.

Heated molding material is then injected into the molding cavity 142 through injector 156. The molding assembly 100 may be heated before or during this portion of the procedure to permit sufficient flow of the molding material to fill the entire molding space 154. The molding material flows through the molding space 154, around the portion of the needle 14 housed therein. The molding material is prevented from entering the needle 14 through its second end 38 due to its abutment with the core 152, which closes off the interior of the needle 14. As a result, the needle 14 becomes embedded in the molding material during this process, without becoming clogged with molding material. Additionally, the second end 38 of the needle 14 is flush with the inner surface of end wall 30 in the finished syringe body 10, because the end of core 152, which defines end wall 30, also determines the position of the needle second end 38.

The molding material is then permitted to cool below its melting point, and in some embodiments may be actively cooled by cooling of the assembly 100, for example by injecting a coolant into cooling channels 150 where provided. Application of the vacuum through vacuum channel 174 is ceased, permitting release of the needle 14 from needle grip 170. Core plates 188 are moved outward in direction D, withdrawing cores 152 from the interiors 20 of the molded syringe bodies 10. Syringe bodies 10 are withdrawn from molding cavities 142 by being moved outward in direction D. At this point the needles 14 have become embedded in the barrels 12 and form integral parts of the syringe bodies 10, such that they are withdrawn from the needle grips 170 when the molded syringe bodies 10 are removed from the assembly 100. Upper portion 110 is then moved upwards, to its original position in preparation for subsequent molding operation, which in turn moves needle blocks 140 inward in direction D, due to their engagement with upper portion 110 by way of posts 116 seated within grooves 182.

A second embodiment of a molding assembly 200 for molding a syringe body 10 in accordance with the invention is shown in FIGS. 20-28. The molding assembly 200 includes a top part 210 and a bottom part 130. In one embodiment, the top part 210 is fixed and the bottom part 230 is mobile, to move the assembly between an opened position, and a closed position, as shown in FIGS. 4-11. In other embodiments the bottom part 130 could be fixed and the top part 210 could be mobile, or both parts could be mobile.

Figure 21:
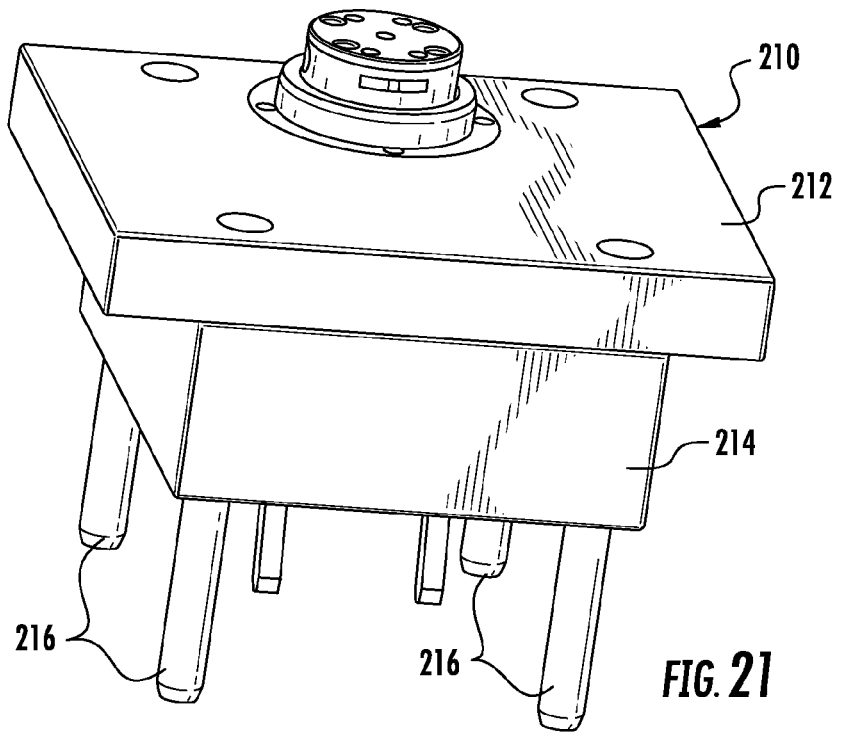
FIG. 21 is a top perspective view of a top part of the molding assembly of FIG. 20.
Figure 22:
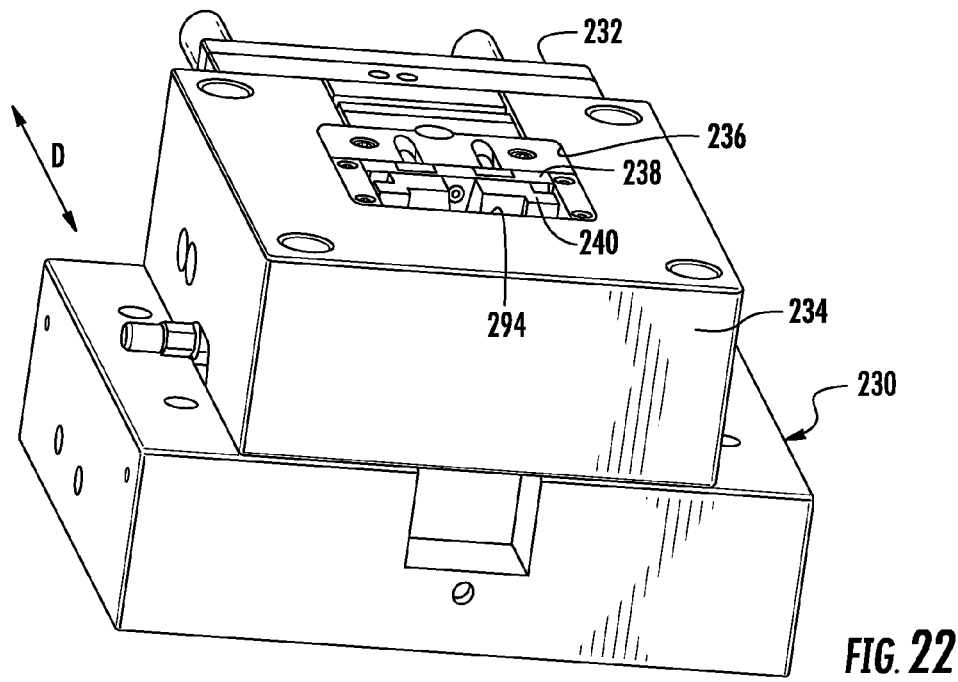
FIG. 22 is a top perspective view of a bottom part of the molding assembly of FIG. 20.
Figure 23:
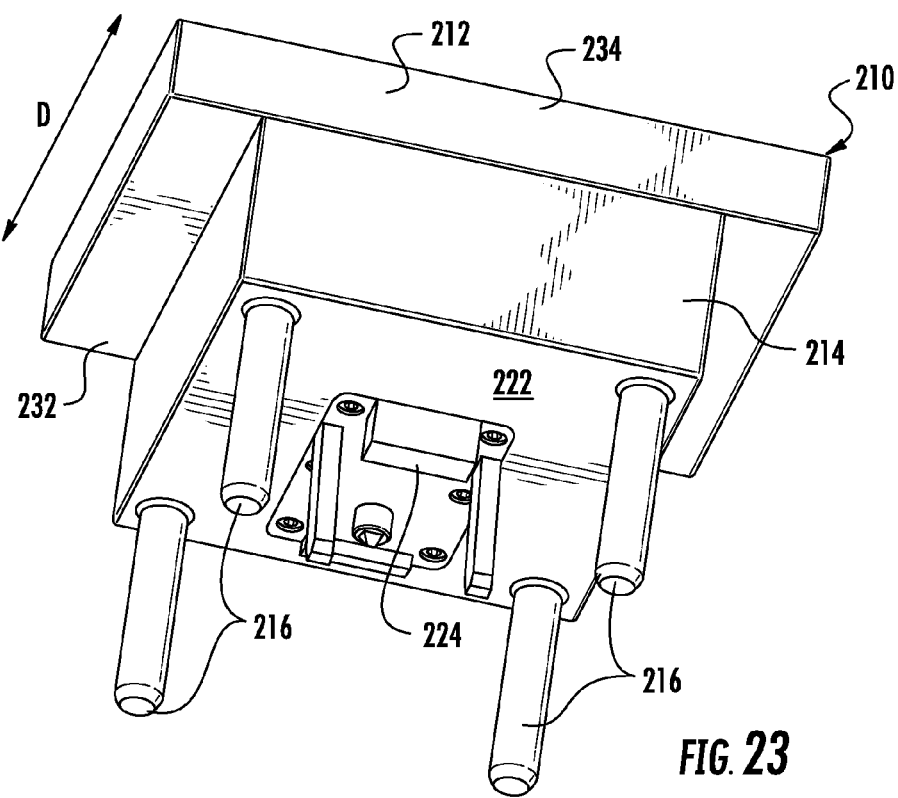
FIG. 23 is a bottom perspective view of the top part of FIG. 21.
Figure 24:
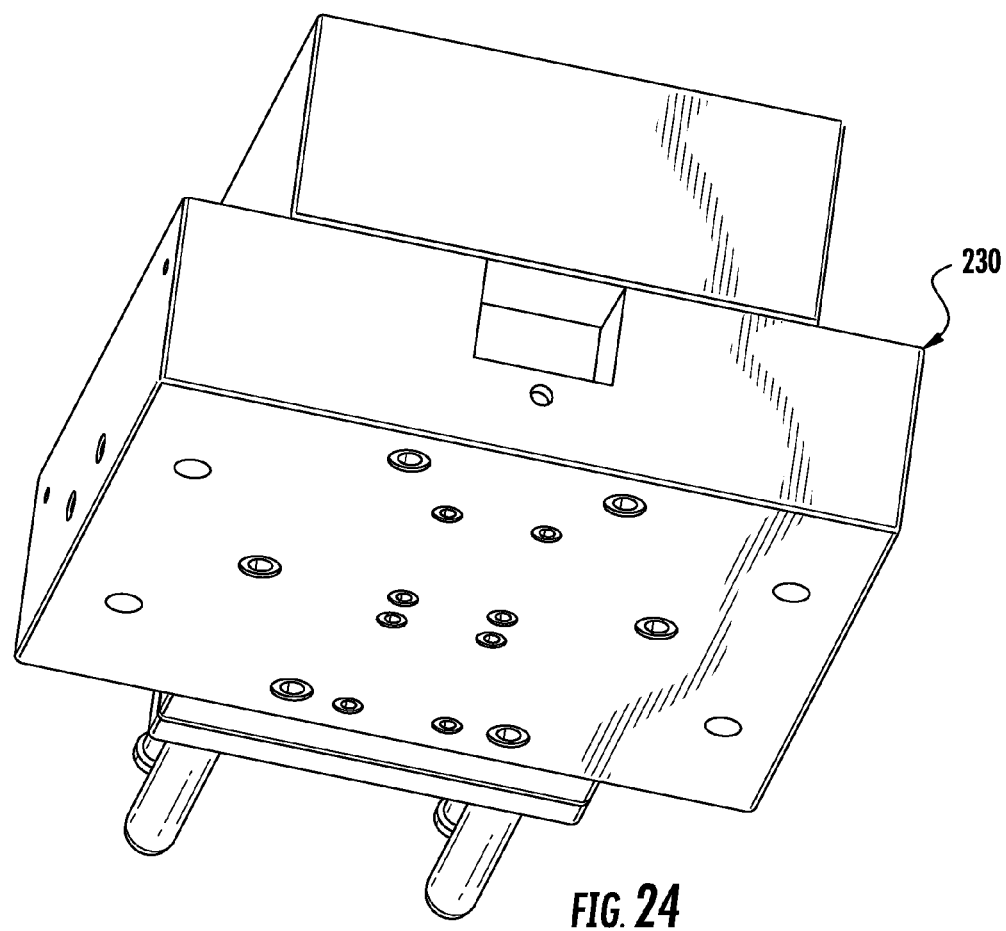
FIG. 24 is a bottom perspective view of the bottom part of FIG. 22.
Figure 25:
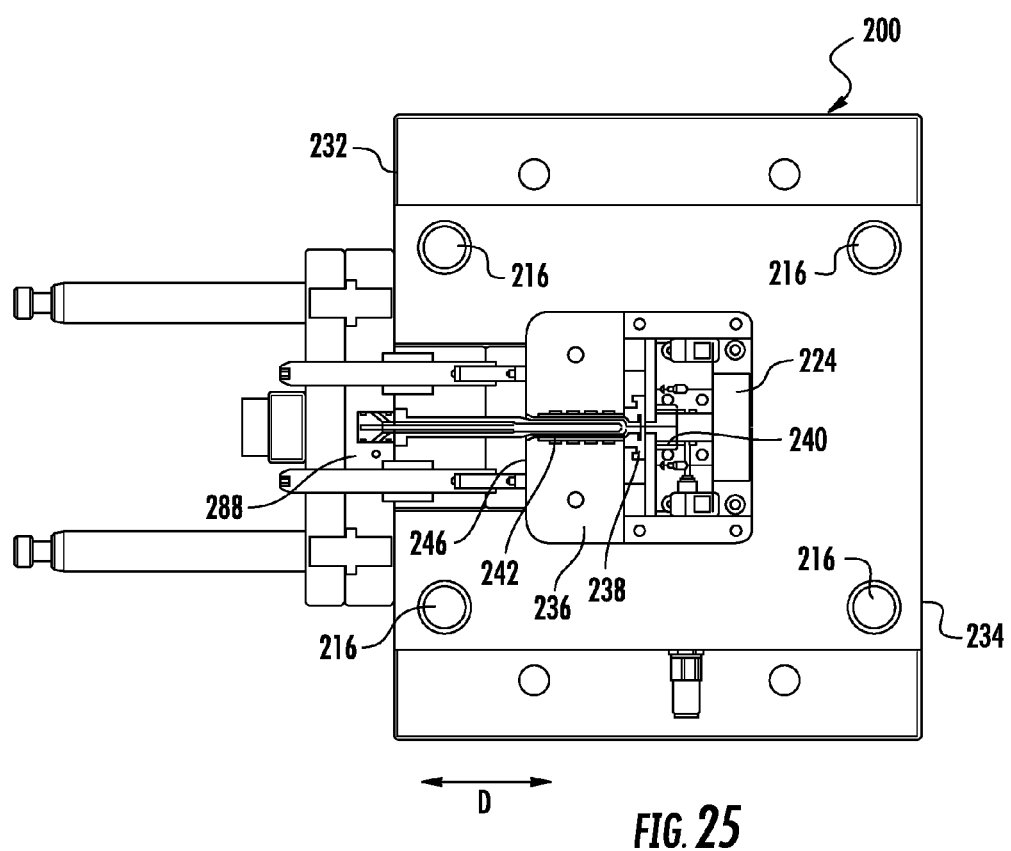
FIG. 25 is a cross section taken along line 25-25 of FIG. 20.

The top part 210 is shown in detail in FIGS. 21 and 23. The top part 210 includes a top plate 212, as shown in FIG. 23. The top plate 212 extends in a substantially horizontal, planar orientation and forms a top surface of the assembly 200. A base member 214 extends downward from the top plate 212 and includes a lower surface 222 positioned to come into abutment with the bottom portion 230. Four posts 216 extend downward from the bottom surface of base member 214 near each of the four corners thereof, for engagement with the bottom portion 230, as described below. A ramp member 224 having a sloped side surface 226 also protrudes downward from the base member 214.

The bottom part 230 is shown in detail in FIGS. 22 and 25-28. As shown, the bottom part 230 includes a molding block 236, an end plate 238, and a needle insertion block 240. The components are arranged such that the molding block 236 is located towards a first end 232 of the bottom part 230 in direction D, the needle insertion block 240 is located towards a second end 234 of the bottom part 230 in direction D, and the end plate 238 is located between the two.

Figure 26:
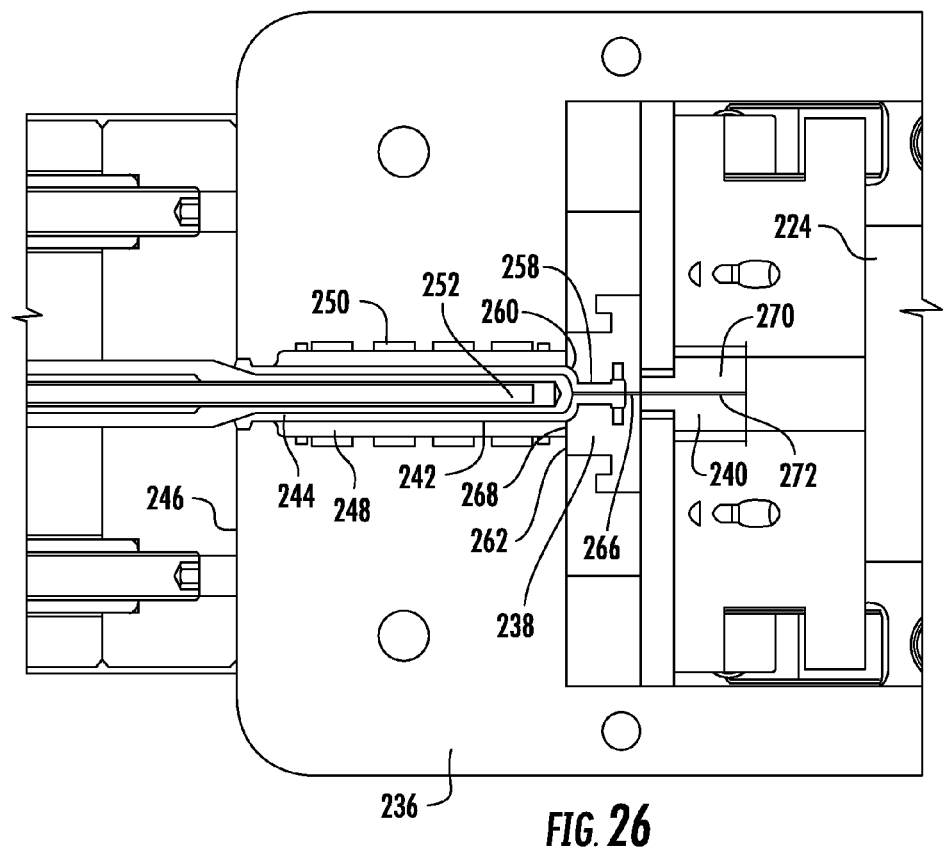
FIG. 26 is an enlarged detail of FIG. 25.
Figure 28:
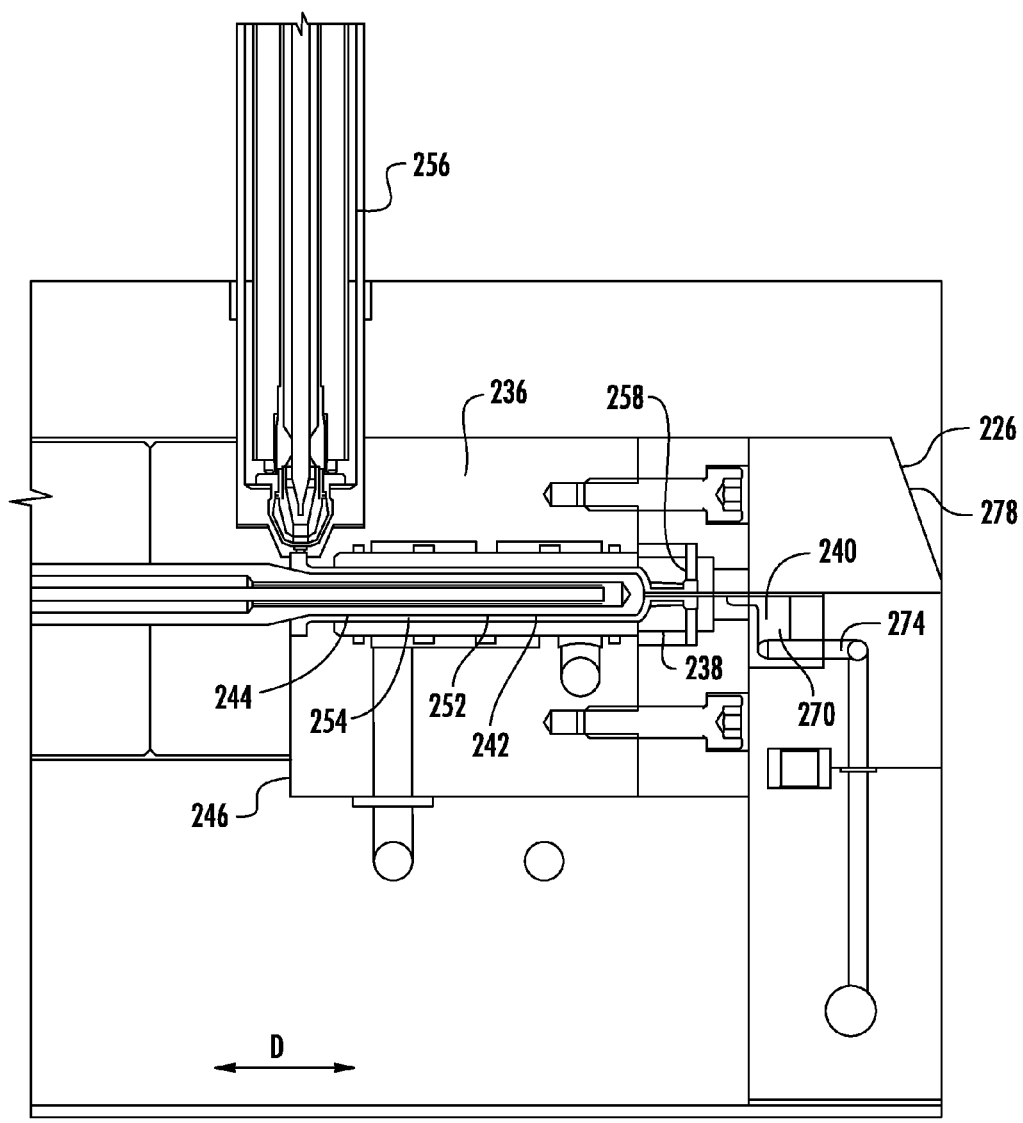
FIG. 28 is an enlarged detail of FIG. 27.

The outer block 236 defines a single molding cavity 242. In other embodiments the outer block 236 could define more molding cavities and the assembly 200 modified to produce multiple syringe bodies 10 during a single molding operation. The molding cavity 242, shown in detail in FIGS. 26 and 28, is configured for molding a syringe barrel 12 of the type shown in FIGS. 1-3. The molding cavity 242 is formed as a cylindrical opening 244 in the molding block 236. The opening 244 extends between a first surface 246 of the molding block 236 that faces towards the first end 232 of the assembly 200 and a second surface 262 of the molding block 236 that faces towards the second end 234 of the assembly 200 in direction D. A sleeve 248 may be fitted within the molding block 236 and define the opening 244. The sleeve 248 is formed of a material capable of appropriately distributing heat during molding and may include a plurality of cooling channels 250.

An inner core 252 fits within the opening 244. The inner core 252 is of a cylindrical shape similar to that of the opening 244, but is of a smaller diameter. A molding space 254 is defined between the opening 244 and the inner core 252. The molding space 254 is sized and shaped to form a syringe barrel 12, such as that shown in FIGS. 1-3. The inner core 252 projects from a core plate 288, which is located towards the first end 232 of the molding assembly 200 in direction D.

Figure 27:
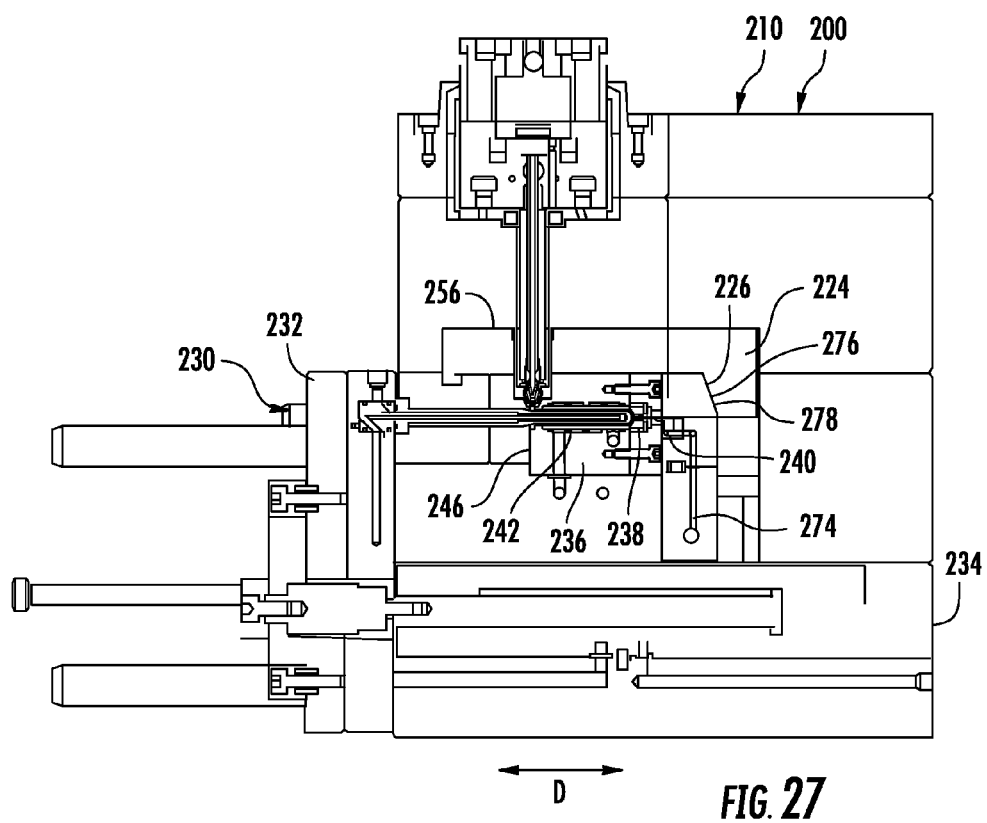
FIG. 27 is a cross section taken along line 27-27 of FIG. 20.

An injector 256 extends through a portion of outer block 236, as shown in FIGS. 27 and 28, for injecting molding material into the molding cavity 242 during molding.

The end plate 238 is shown in detail in FIGS. 25-28. The end plate 238 abuts the first surface 246 of molding block 236 when the molding assembly 200 is in a closed position. The end plate 238 defines a hub cavity 258 that forms the hub 24 of the syringe body 10. Hub cavity 258 includes an opening 260 defined on the second surface 262 of the end plate 238, which faces towards the first end 232 of the molding assembly 200 in direction D and abuts the first surface 246 of the molding block 236. Hub cavity 258 is axially aligned with molding cavity 242, to define a continuous, barrel-shaped cavity for forming the syringe barrel 12. The portion of molding space 254 that forms the barrel end wall 30 is defined between curved portions of end plate second surface 262 and the end of core 252. A passage 266 extends from hub cavity 258 to a surface 268 of end plate 238, which faces towards the second end 234 of the molding assembly 200 in direction D.

The needle holding block 240 is located towards the second end 234 of the molding assembly 200 in direction D, with respect to the end plate 238. A needle grip 270 is housed within an opening formed on a surface 190 of the needle holding block 240, which faces towards the first end 232 of the molding assembly 200 in direction D. The needle grip 270 includes a needle opening 272 that is sized and shaped to receive a portion of the needle 14 located towards the first end 34 thereof, but is sufficiently large so as to not create an interference fit between the needle 14 and the opening 272, so as to allow some sliding of the needle 14, as described below. The needle opening 272 is axially aligned with the molding cavity 242 and the needle passage 266, when the molding assembly 200 is in the closed position.

A vacuum channel 274 extends through the needle holding block 240 and is in communication with the needle opening 272.

A surface 276 of the needle holding block 240 that faces towards the second end 232 of the molding assembly 200 in direction D includes a sloped surface 278 that is complementary with the sloped side surface 226 of ramp member 224.

Figure 20:
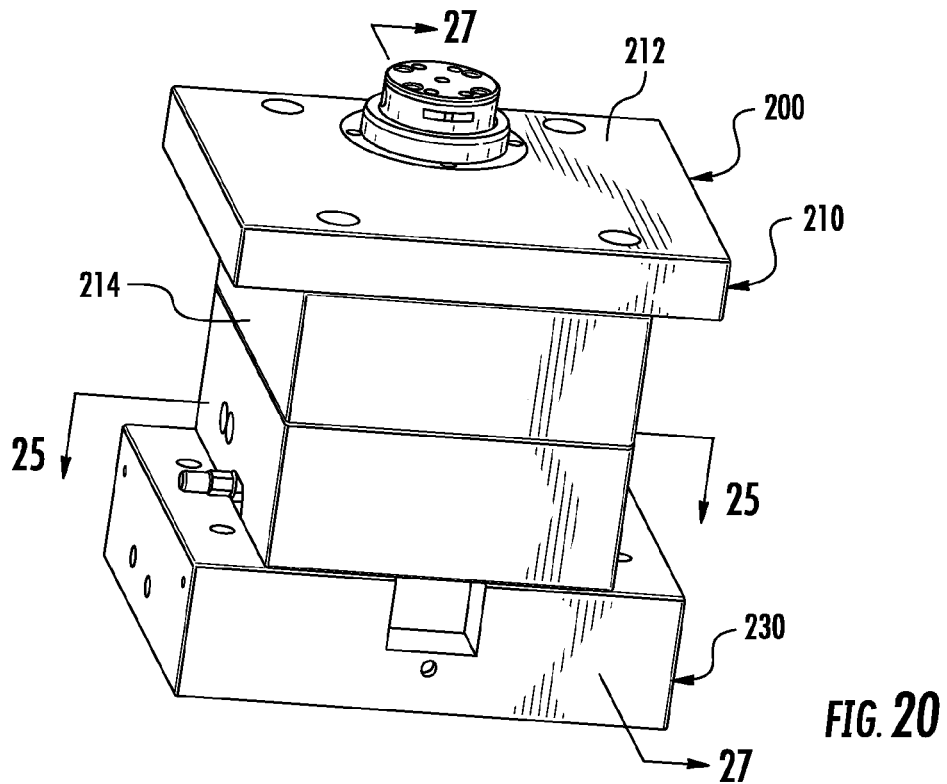
FIG. 20 is a top perspective view of a second embodiment of a molding assembly in accordance with the invention, in a closed position.

A syringe body 10 in accordance with the invention is molded using the molding assembly 200 as follows. The top part 210 of the assembly 200 is initially held in a raised position with respect to the bottom part 230. Posts 216 are slidably engaged with complementary holes 282 formed in base member 214 to retain top part 210 and bottom part 230 in alignment, as shown in FIG. 20. A needle 14 is placed within the opening 272 of the needle grip 270, oriented with the first end 34 having the staked tip 36 pointing towards the first end 232 of the assembly 200 in direction D, and the second end 38 pointing towards the second end 234 of the assembly 200 in direction D. At this time, the core plate 188 is located towards the second end 234 of the assembly 200 in direction D, and the core 252 is located outside of the opening 244.

Upon initiation of a molding operation, core plate 288 is first moved towards the second end 234 of the assembly in direction D, such that the core 252 is moved into opening 244 to create a syringe barrel 12 shaped molding space. 254. After the core 252 is in position, the needle 14 is moved into a molding position, as shown in FIGS. 25-28. During this time, a vacuum is applied to opening 272 through the vacuum channel 274. This vacuum slidably secures the needle 14 within the opening 272. To move the needle 14 into the molding position, top part 210 of the molding assembly 200 is moved downward, towards the bottom part 230, or bottom part 230 is moved upwards towards the top part 210. Engagement of posts 216 within holes 282 guides the top part 210 and bottom part 230 towards each other. Ramp member 224 enters a space 294 adjacent to the needle holding block 240 and located towards the second end 234 of the assembly 200 with respect thereto. Sloped side surface 226 of ramp member 224 comes into contact with sloped side 278 of needle holding block 240, which drives needle holding block 240 in direction D, towards the first end 232 of the assembly 20, which results in the needle 14 held within needle grip 270 being driven towards the core 252 in direction D. Needle 14 continues to move until it comes into abutment with core 252, as shown in FIGS. 25-28. The slidabilty of needle 14 within opening 272 allows the needle 14 to be precisely positioned against the core 252, as needle grip 270 can continue to move in direction D towards the first end 232 of the assembly 200 after needle 14 has come into position and is prevented from further movement by the core 252. Needle grip 270 continues to move towards first end 232 in direction D, until it comes into abutment with end plate 238, closing off the molding cavity 242 and the molding space 254.

Heated molding material is then injected into the molding cavity 242 through injector 256. The molding assembly 200 may be heated before or during this portion of the procedure to permit sufficient flow of the molding material to fill the entire molding space 254. The molding material flows through the molding space 254, around the portion of the needle 14 housed therein. The molding material is prevented from entering the needle 14 through its second end 38 due to its abutment with the core 252, which closes off the interior of the needle 14. As a result, the needle 14 becomes embedded in the molding material during this process, without becoming clogged with molding material. Additionally, the second end 38 of the needle 14 is flush with the inner surface of end wall 30 in the finished syringe body 10, because the end of core 152, which defines end wall 30, also determines the position of the needle second end 38.

The molding material is then permitted to cool below its melting point, and in some embodiments may be actively cooled by cooling of the assembly 200, for example by injection a coolant into cooling channels 250 where provided. Application of the vacuum through vacuum channel 274 is ceased, permitting release of the needle 14 from the needle grip 270. Core plate 288 is moved towards the first end 232 of the assembly 200 in direction D, withdrawing core 252 from the interior 20 of molded syringe body 10. Syringe body 10 is withdrawn from molding cavity 242 by being moved outward therefrom, towards the first end 232 of the assembly in direction D. At this point the needle 14 has become embedded in the barrel 12 and forms an integral part of the syringe body 10, such that it is withdrawn from needle grip 170 when the molded syringe body 10 is removed from the assembly 200. Top part 210 is then moved upwards, or bottom part 230 moved downwards, and needle holding block 240 is moved back towards the first end 232 of the assembly 200 in direction D, to permit a subsequent molding operation to take place.

While the preferred embodiments of the invention have been described in detail above, the invention is not limited to the specific embodiments described, which should be considered as merely exemplary.

What is claimed is:

1. A molding assembly for molding a syringe with a needle embedded therein, the assembly, comprising:
   a first mold portion comprising a top plate and a plug member extending downward from a bottom surface thereof;
   a second mold portion comprising a molding block, an end plate, and a needle holding block configured to hold the needle;
   wherein, the assembly moves between an opened position in which the first mold portion is displaced from the second mold portion, and a closed position in which the molding block and the end plate define a molding cavity configured to form a body portion of the syringe, and the first mold portion contacts the second mold portion to hold the needle holding block adjacent to the molding cavity, such that the needle is partially positioned within the molding cavity.

2. The molding assembly of claim 1, wherein the first mold portion is located above the second mold portion.

3. The molding assembly of claim 1, wherein the plug member drives the needle holding block towards the end plate when the assembly is moved into the closed position.

4. The molding assembly of claim 1, wherein the molding block and the end plate define a plurality of molding cavities.

5. The molding assembly of claim 1, wherein the molding cavity has a substantially cylindrical shape.

6. The molding assembly of claim 1, wherein the molding block defines a cylindrical syringe barrel body portion of the molding cavity, and the end plate defines a syringe barrel hub portion of the molding cavity.

7. The molding assembly of claim 1, wherein a sleeve is fitted within the molding cavity.

8. The molding assembly of claim 7, wherein the sleeve comprises a plurality of cooling channels.

9. The molding assembly of claim 1, further comprising an inner core that fits within the molding cavity to define an interior of the body portion of the syringe.

10. The molding assembly of claim 9, wherein the inner core is located within the molding cavity when the assembly is in the closed position and outside of the molding cavity when the assembly is in the opened position.

11. The molding assembly of claim 9, wherein the inner core projects from a core plate that moves towards the assembly when the assembly moves into the closed position, and away from the assembly when the assembly moves into the opened position.

12. The molding assembly of claim 1, further comprising an injector for injecting a molding material into the molding cavity during a molding operation.

13. The molding assembly of claim 12, wherein the injector extends through the molding block, to the molding cavity.

14. The molding assembly of claim 9, wherein the needle contacts the core when the assembly is in the closed position.

15. The molding assembly of claim 14, wherein the needle comprises a first, staked end for injecting into a patient, and a second end that comes into abutment with an end of the core when the assembly is in the closed position.

16. The molding assembly of claim 1, wherein the needle holding block comprises a needle grip, the needle grip having a needle grip opening configured to slidably house the needle and axially aligned with the molding cavity to position the needle at a closed end of the body portion of the syringe.

17. The molding assembly of claim 16, further comprising a vacuum channel in communication with the needle grip opening.

18. The molding assembly of claim 17, wherein the vacuum channel extends through the needle holding block.

19. The molding assembly of claim 17, wherein the vacuum channel applies a vacuum to the needle grip opening during molding to slidably secure the needle within the needle grip opening.

20. A method of molding a syringe using the molding assembly of claim 1, comprising:
   providing the molding assembly in the opened position;
   moving the molding assembly into the closed position by moving the first mold portion into contact with the second mold portion and locating a portion of the needle within the molding cavity;
   injecting a molding material into the molding cavity;
   cooling the molding material to solidify the molding material and produce a syringe body with the needle embedded therein;
   moving the molding assembly into the opened position; and
   removing the syringe body from the molding assembly.

21. The method of claim 20, wherein moving the molding assembly to the closed position further comprises moving an inner core into the molding cavity to define an interior portion of the syringe body.

22. The method of claim 21, further comprising positioning the needle in abutment with the core when the assembly is in the closed position.

23. The method of claim 22, wherein the needle comprises a first end having a staked tip and a second end, the second end being in abutment with an end of the core when the assembly is in the closed position.

24. The method of claim 20, wherein the needle holding block comprises a needle grip having an opening and a vacuum channel, the method further comprising slidably holding the needle within the opening by application of a vacuum through the vacuum channel.

25. A syringe produced using the molding assembly of claim 1, the syringe comprising:
   a barrel formed as a substantially tubular wall having a first, opened end leading to an interior and a second, closed end;
   a hub extending outward from the second end; and
   a needle extending through the hub, the needle having a first, staked end for injecting into a patient, and a second end located on the interior and flush with an inner surface of the barrel.

26. The molding assembly of claim 1, wherein the molding block and the end plate define a continuous, barrel-shaped molding cavity.

27. The molding assembly of claim 1, wherein the needle holding block comprises a needle grip.

28. A molding assembly for molding a syringe with a needle embedded therein, the assembly, comprising:
   a first mold portion;
   a second mold portion comprising a molding block, an end plate, and a needle holding block configured to hold the needle;
   wherein, the assembly moves between an opened position in which the first mold portion is displaced from the second mold portion, and a closed position in which the molding block and the end plate define a molding cavity configured to form a body portion of the syringe, and the first mold portion contacts the second mold portion to hold the needle holding block adjacent to the molding cavity, such that the needle is partially positioned within the molding cavity; and wherein the second mold portion comprises a plurality of sides, each side comprising a molding block, an end plate, and a needle holding block configured to hold the needle, wherein the assembly moves between an opened position in which the first mold portion is displaced from the second mold portion, and a closed position in which the molding block and the end plate of each side define a molding cavity configured to form a body portion of the syringe, and the first mold portion contacts the second mold portion to hold the needle holding blocks adjacent to the molding cavities, such that the needles are partially positioned within the molding cavities.

29. The molding assembly of claim 28, wherein the second mold portion comprises two sides that are arranged in a linear alignment with each other and extend outward from a central region of the assembly as mirror images of each other.

30. The molding assembly of claim 29, wherein the first portion is located between the two second portions.

31. The molding assembly of claim 30 wherein the first portion comprises a top plate and a plug member extending downward from a bottom surface thereof, wherein the plug member is located between the needle holding blocks of the two sides when in the closed position.

32. The molding assembly of claim 31, wherein the plug member and the needle holding blocks comprise complementary angled sides.

33. The molding assembly of claim 32, wherein the plug member has an inverted frusto-pyramidal shape.

34. The molding assembly of claim 31, wherein the plug member moves the needle holding blocks in outward directions with respect to the assembly, towards the end plates, when the assembly is moved from the opened position to the closed position.

35. The molding assembly of claim 34, wherein the first mold portion comprises a plurality of posts extending downward at selected angles with respect to the assembly, and the needle holding blocks comprise grooves on outer surfaces thereof and extending downward at the selected angles, and the posts slidably engage the grooves to move the needle holding blocks in the outward directions when the assembly is moved from the opened position to the closed position.

36. A molding assembly for molding a syringe with a needle embedded therein, the assembly, comprising:
a first mold portion;
a second mold portion comprising a molding block, an end plate, and a needle holding block configured to hold the needle;
wherein, the assembly moves between an opened position in which the first mold portion is displaced from the second mold portion, and a closed position in which the molding block and the end plate define a molding cavity configured to form a body portion of the syringe, and the first mold portion contacts the second mold portion to hold the needle holding block adjacent to the molding cavity, such that the needle is partially positioned within the molding cavity; and
wherein the first mold portion comprises a top plate and a base member having a lower surface positioned to come into contact with the second mold portion when the assembly is in the closed position.

37. A molding assembly for molding a syringe with a needle embedded therein, the assembly, comprising:
a first mold portion;
a second mold portion comprising a molding block, an end plate, and a needle holding block configured to hold the needle;
wherein, the assembly moves between an opened position in which the first mold portion is displaced from the second mold portion, and a closed position in which the molding block and the end plate define a molding cavity configured to form a body portion of the syringe, and the first mold portion contacts the second mold portion to hold the needle holding block adjacent to the molding cavity, such that the needle is partially positioned within the molding cavity; and
wherein the first mold portion comprises a plurality of posts that are slidably received by openings formed in the second mold portion.

38. The molding assembly of claim 36, wherein the first mold portion further comprises a ramp member having a first sloped surface and extending downward from the lower surface of the base member.

39. The molding assembly of claim 38, wherein the needle holding block comprises a second sloped surface that is complementary with the first sloped surface.

40. The molding assembly of claim 39, further comprising a space adjacent to the needle holding block when the assembly is in the closed position, wherein the ramp member enters the space when the assembly moves into the closed position and the first sloped surface engages the second sloped surface to move the needle holding block towards the molding cavity.

* * * * *